US008481000B2

(12) United States Patent
Holahan

(10) Patent No.: US 8,481,000 B2
(45) Date of Patent: Jul. 9, 2013

(54) THICKENED BEVERAGES FOR DYSPHAGIA

(75) Inventor: John L. Holahan, St. Louis, MO (US)

(73) Assignee: Simply Thick, LLC, St. Louis, MO (US)

( * ) Notice: Subject to any disclaimer, the term of this patent is extended or adjusted under 35 U.S.C. 154(b) by 1968 days.

(21) Appl. No.: 10/542,506

(22) PCT Filed: Jan. 31, 2004

(86) PCT No.: PCT/US2004/002795
§ 371 (c)(1),
(2), (4) Date: Jul. 15, 2005

(87) PCT Pub. No.: WO2004/069179
PCT Pub. Date: Aug. 19, 2004

(65) Prior Publication Data
US 2006/0051296 A1 Mar. 9, 2006

Related U.S. Application Data

(60) Provisional application No. 60/444,079, filed on Jan. 31, 2003, provisional application No. 60/443,941, filed on Jan. 31, 2003, provisional application No. 60/444,080, filed on Jan. 31, 2003, provisional application No. 60/444,082, filed on Jan. 31, 2003.

(51) Int. Cl.
A61K 51/00 (2006.01)
A61M 36/14 (2006.01)

(52) U.S. Cl.
USPC .......................................... 424/1.11; 426/590

(58) Field of Classification Search
USPC .............. 424/1.11, 1.65; 426/2, 66, 589, 594, 426/597, 592, 590, 599, 580
See application file for complete search history.

(56) References Cited

U.S. PATENT DOCUMENTS

| 2,440,365 | A |   | 4/1948  | Copping et al. |
|-----------|---|---|---------|----------------|
| 3,201,317 | A |   | 8/1965  | Miller |
| 3,750,908 | A |   | 8/1973  | Bauerlein et al. |
| 3,773,752 | A |   | 11/1973 | Buchanan et al. |
| 3,830,407 | A | * | 8/1974  | Wierlo ........................ 222/145.6 |
| 3,949,104 | A |   | 4/1976  | Cheng et al. |
| 4,010,071 | A |   | 3/1977  | Colegrove |
| 4,107,343 | A |   | 8/1978  | Petricca |
| 4,135,979 | A |   | 1/1979  | Corley et al. |
| 4,229,825 | A |   | 10/1980 | Guidoux |
| 4,252,835 | A |   | 2/1981  | Maerker et al. |
| 4,269,974 | A |   | 5/1981  | Wintersdorff |
| 4,299,825 | A |   | 11/1981 | Lee |
| 4,427,681 | A |   | 1/1984  | Munshi |
| 4,654,086 | A |   | 3/1987  | Baird et al. |
| 4,670,550 | A |   | 6/1987  | Bleeker et al. |
| 4,671,966 | A |   | 6/1987  | Giddey et al. |
| 4,689,219 | A |   | 8/1987  | Sugden |
| 4,774,093 | A |   | 9/1988  | Provonchee et al. |
| 4,828,724 | A |   | 5/1989  | Davidson |
| 4,855,156 | A |   | 8/1989  | Singer et al. |
| 4,859,484 | A |   | 8/1989  | Bielskis et al. |
| 4,894,335 | A |   | 1/1990  | Peignier et al. |
| 5,202,146 | A |   | 4/1993  | Singer et al. |
| 5,251,699 | A |   | 10/1993 | Lau et al. |
| 5,270,459 | A |   | 12/1993 | Shatzman et al. |
| 5,300,302 | A |   | 4/1994  | Tachon et al. |
| 5,338,561 | A |   | 8/1994  | Campbell et al. |
| 5,362,713 | A |   | 11/1994 | Westland et al. |
| 5,385,748 | A |   | 1/1995  | Bunger et al. |
| 5,536,825 | A |   | 7/1996  | Yeh et al. |
| 5,633,028 | A |   | 5/1997  | Wong |
| 5,648,093 | A |   | 7/1997  | Gole et al. |
| 5,654,027 | A |   | 8/1997  | Chalupa |
| 5,811,148 | A |   | 9/1998  | Chiu et al. |
| 5,837,272 | A |   | 11/1998 | Fierro, Jr. et al. |
| 5,869,029 | A |   | 2/1999  | Graff-Andersen et al. |
| 5,932,235 | A |   | 8/1999  | Ninomiya et al. |
| 5,976,084 | A |   | 11/1999 | Tymchuck |
| 5,997,907 | A |   | 12/1999 | Goswami et al. |
| 6,001,408 | A |   | 12/1999 | Dudacek et al. |
| 6,007,848 | A |   | 12/1999 | Hendrick et al. |
| 6,033,712 | A |   | 3/2000  | Greenshields et al. |
| 6,033,713 | A |   | 3/2000  | Sheldon |
| 6,036,982 | A |   | 3/2000  | Lehmberg et al. |
| 6,139,895 | A |   | 10/2000 | Zablocki et al. |
| 6,149,962 | A |   | 11/2000 | Loh et al. |
| 6,162,471 | A |   | 12/2000 | Sheldon |

(Continued)

FOREIGN PATENT DOCUMENTS

DE  19918210 A1  11/2000
EP  0130771     1/1985

(Continued)

OTHER PUBLICATIONS

Castellanos, V. H., PHD, RD; Butler, E. RD; Gluch, L., RD; Burke, B., RD, Use of Thickened Liquids in Skilled Nursing Facilities, Jrnl of the Amer Dietetic Association Aug. 2004. NYEEI: Otolaryngology: FAQS About Swallowing Disorders, Online NYEEI: http://www.nyee.edu/faqlist.html?tablename=faz& key=48&print=.

Deis, Ronald C., Ph.D., Dietary Fiber: A Healthy Discussion, Weeks Publishing Co, Jan. 1999, Design Elements Online, http://www.foodproductdesign.com/archive/1990/0199de.html.

Edmonds, C., M.R.C.P. D.P.M., Huntington's CORA, Dysphagia and Death, The Medical Journal of Australia, Aug. 6, 1966.

Department of Health and Human Services, FDA; 21 CFR Part 201 (DKT 90N0364 RIN0905-AD91, Regulation of Medical Foods: Advance Notice of Proposed Rulemaking, Federal Register, vol. 61. U.S. Food and Drug Administration Center for Food Safety and Applied Nutrition [Online] http://www.cfsan.fda.gov/-dms/ds-medfd.html Aug. 24, 2001.

(Continued)

Primary Examiner — D L Jones
(74) Attorney, Agent, or Firm — Polster Lieder Woodruff & Lucchesi, L.C.

(57) ABSTRACT

The present invention relates to thickened beverage compositions. More particularly the invention relates to beverage compositions thickened for the management of dysphagia. More particularly this invention relates to the production of thickened beverages by a dispensing machine that is also capable of dispensing non-thickened beverages.

7 Claims, 3 Drawing Sheets

U.S. PATENT DOCUMENTS

| | | | |
|---|---|---|---|
| 6,174,549 B1 | 1/2001 | Greenshields et al. | |
| 6,200,623 B1 | 3/2001 | Dudacek et al. | |
| 6,277,395 B1 | 8/2001 | Fukui et al. | |
| 6,455,090 B1 * | 9/2002 | Uzuhashi et al. | 426/573 |
| 6,458,395 B1 | 10/2002 | Emoto | |
| 6,461,589 B2 | 10/2002 | Robbins | |
| 6,559,187 B2 | 5/2003 | Chandran | |
| 6,686,341 B1 | 2/2004 | Bijlsma et al. | |
| 7,638,150 B2 * | 12/2009 | Holahan | 426/2 |
| 2004/0197456 A1 | 10/2004 | Holahan | |

FOREIGN PATENT DOCUMENTS

| | | |
|---|---|---|
| EP | 0620012 A1 | 10/1994 |
| EP | 1046347 A1 | 10/2000 |
| EP | 1078981 A1 | 2/2001 |
| JP | 06040950 A | 2/1994 |
| JP | 07274915 A | 10/1995 |
| JP | 10229517 | 5/1999 |
| JP | 11124342 A | 5/1999 |
| JP | 11124342 L | 5/1999 |
| JP | 1187827 | 7/1999 |
| JP | 11187827 A | 7/1999 |
| JP | 11187827 L | 7/1999 |
| JP | 10131478 | 11/1999 |
| JP | 11318356 | 11/1999 |
| JP | P200041594 A | 2/2000 |
| JP | P200041594 L | 2/2000 |
| JP | 2000135070 A | 5/2000 |
| JP | 2000325041 A | 11/2000 |
| WO | WO 9934690 | 1/1998 |
| WO | WO 9925208 | 5/1999 |
| WO | WO 0057727 A1 | 5/2000 |
| WO | 9934690 | 10/2000 |
| WO | WO 0115743 A2 | 3/2001 |
| WO | 0179521 A1 | 10/2001 |
| WO | WO 0211716 A2 | 2/2002 |
| WO | WO 03011051 A1 | 2/2003 |

OTHER PUBLICATIONS

Lontong, V.; Texture and Flavor Characteristics of Beverages Containing Commercial Thickening Agents for Dysphagia Diets, Journal of Food Science, vol. 68, Nov. 4, 2003 1537-1541.

PCT Notification of Transmittal of the International Search Report or the Declaration, International Application No. PCT/US02/24525, Date of Mailing Dec. 2, 2002; 6 pages.

International Search Report, 02759246.8-1221-US02/24525, P71214EP00, 4 pages.

Xanthan gum, G. Sworn, Monsanto (Kelco Biopolymers, Tadworth), in Handbook of Hydrocolloids, ed. G.O. Phillips and P. Williams, Woodhead Publishing Ltd, Cambridge, England, Jul. 2000, pp. 103-115. Available at: http://docencia.izt.uam.mx/epa/quim_alim/tareas/xantana.pdf.

Australian Examiner's report No. 4 on patent application No. 2002324592 dated Mar. 28, 2008 (4 pgs.).

Department of Health and Human Services; Food & Drug Administration; Warning Statements Required for Over-The-Counter Drugs Containing Water-Soluble Gums as Active Ingredients.

Federal Register; vol. 58, No. 164; Thursday, Aug. 26, 1993/Rules and Regulations (8 pages total).

American College of Radiology; ACR Appropriateness Criteria; "Imaging Recommendations for Patients with Dysphagia"; p. 225-230 (6 pages total).

American Speech-Language Hearing Association; "Communication Facts, Special Populations: Dysphagia"; 1999 Edition (3 pages total).

Dysphagia 9:209-217; "Epidemiology and Dysphagia"; Keith V. Kuhlemeier, PhD, MPH; 1994; p. 209-217 (9 pages total).

American Speech-Language Hearing Association; "Communication Facts, Special Populations: Dysphagia"; 2001 Edition; http://professional.asha.org/research/dysphagia.htm (6 pages total).

Journal of Neuroscience Nursing, Apr. 1989, vol. 21, No. 2; "Dysphagia in Huntington's Disease"; Vicki P. Hunt, RN, Francis O. Walker, MD; p. 92-95 (4 pages total).

Arch Neurol—vol. 42, Jan. 1985; "Dysphagia in Huntington's Disease"; Norman A. Leopold, DO, Marion C. Kagel, MA; p. 57-60 (4 pages total).

Abstract; Research Disclosure, XP-002305761; "Concentrated Gellan Gum Gel (5%)Suitable to Gel Various Other Systems"; King, A.H.; 1996 (1 page total).

English Translation of Published Japanese Patent Application No. JP11187827A (16 pgs.).

Canadian Examiner's Notice of Allowance on patent application No. 2509715 dated Oct. 26, 2009 (1 pg.).

American Speech-Language Hearing Association; "Special Populations: Stroke"; 2002 Edition; http://professional.asha.org/research/dysphagia.htm (6 pgs.).

Applied microbiology and biotechnology, Aug. 1998, vol. 50, No. 2, "Xanthan gum biosynthesis and application:a biochemical /genetic perspective", A. Becker á F. Katzen á A. PuÈ hler á L. Ielpi, p. 145-152 (8 pgs.).

Art. 96(2) EPC Communication, European Application No. 027596246.8, Date of Mailing Apr. 10, 2007, (5 pgs.).

Art. 96(2) EPC Communication, European Application No. 027596246.8, Date of Mailing Nov. 13, 2007, (3 pgs.).

Art. 94(3) EPC Communication, European Application No. 027596246.8, Date of Mailing Apr. 16, 2008, (6 pgs.).

Art. 94(3) EPC Communication, European Application No. 027596246.8, Date of Mailing Nov. 13, 2008, (3 pgs.).

Art. 96(2) EPC Communication, European Application No. 04707165.9, Date of Mailing Aug. 7, 2006, (5 pgs.).

Art. 94(3) EPC Communication, European Application No. 04707165.9, Date of Mailing Apr. 7, 2008, (5 pgs.).

Australian Examiner's report No. 5 on patent application No. 2002324592 dated Apr. 30, 2008 (3 pgs.).

Australian Examiner's report No. 6 on patent application No. 2002324592 dated Jun. 5, 2008 (3 pgs.).

Canadian Examiner's Notice of Allowance on patent application No. 2459924 dated Feb. 23, 2009 (1 pg.).

Canadian Examiner's Requisition on patent application No. 2459924 dated Jul. 21, 2005 (4 pgs.).

Canadian Examiner's Requisition on patent application No. 2459924 dated Apr. 3, 2006 (4 pgs.).

Canadian Examiner's Requisition on patent application No. 2459924 dated Nov. 29, 2006 (4 pgs.).

Canadian Examiner's Requisition on patent application No. 2459924 dated Sep. 7, 2007 (3 pgs.).

Canadian Examiner's Requisition on patent application No. 2459924 dated Apr. 22, 2008 (5 pgs.).

Canadian Examiner's requisition on patent application No. 2509715 dated Feb. 19, 2009 (3 pgs.).

Compiled by a Castrogiovanni, Communication Facts: Special Populations: Dysphagis BO 2002 Edition, ASHA Resource Center, http://professional.asha.org/research/dysphagia.html (3 pgs.).

Decision to Grant EPC Communication, European Application No. 04707165.9, Date of Mailing Dec. 30, 2008, (2 pgs.).

European Search Report, European Application No. 027596246.8, Date of Mailing Aug. 12, 2004, (4 pgs.).

European Search Report, European Application No. 04707165.9, Date of Mailing Jan. 27, 2006, (4 pgs.).

European Search Report, European Application No. 09005203.6, Date of Mailing Aug. 12, 2004, (6 pgs.).

Intent to Grant EPC Communication, European Application No. 04707165.9, Date of Mailing Apr. 27, 2009, (32 pgs.).

Intent to Grant EPC Communication, European Application No. 04707165.9, Date of Mailing Jul. 28, 2008, (33 pgs.).

PCT Notification of Transmittal of International Preliminary Examination Report, International Application No. PCT/US02/24525, Date of Mailing Aug. 23, 2004; (5 pgs.).

PCT Notification of Transmittal of the International Search Report or the Declaration, International Application No. PCT/US02/24525, Date of Mailing Dec. 2, 2002; (6 pgs.).

Written Opinion of the International Searching Authority, International Application No. PCT/US02/24525, Date of Mailing Feb. 18, 2004; (5 pgs.).

Ikegami, S. et al., "Effect of viscous indigestible polysaccharides on pancreatic-biliary secretion and digestive organs in rats", Journal of Nutrition, 120, pp. 353-360, 1990.

Dietary Fiber Definition Committee, "The definition of dietary fibre", Cereal Foods World, 46, pp. 112-126, Mar. 2001.

Jenkins, D.J.A. etal., "Dietary fibres, fibre analogues, and glucose tolerance: importance of viscosity", British Medical Journal, 1, pp. 1392-1394, May 27, 1978.

Torsdottir, I. etal., "A small dose of soluble alginate-fiber affects postprandial glycemia and gastric emptying in humans with diabetes", Journal of Nutrition, 121, pp. 795-799, 1991.

Jenkins, D.J.A. etal., "Unabsorbable carbohydrates and diabetes: decreased post-prandial hyperglycaemia", The Lancet, 308, pp. 172-174, Jul. 24, 1976.

Wolever, T.M.S. etal., "Guar gum and reduction of post-prandial glycaemia: effect of incorporation into solid food, liquid food, and both", British Journal of Nutrition, 41, pp. 505-510, 1979.

Reppas, C. etal., "High viscosity hydroxypropylmethylcellulose reduces postprandial blood glucose concentrations in NIDDM patients", Diabetes Research and Clinical Practice, 22, pp. 61-69, 1993.

* cited by examiner

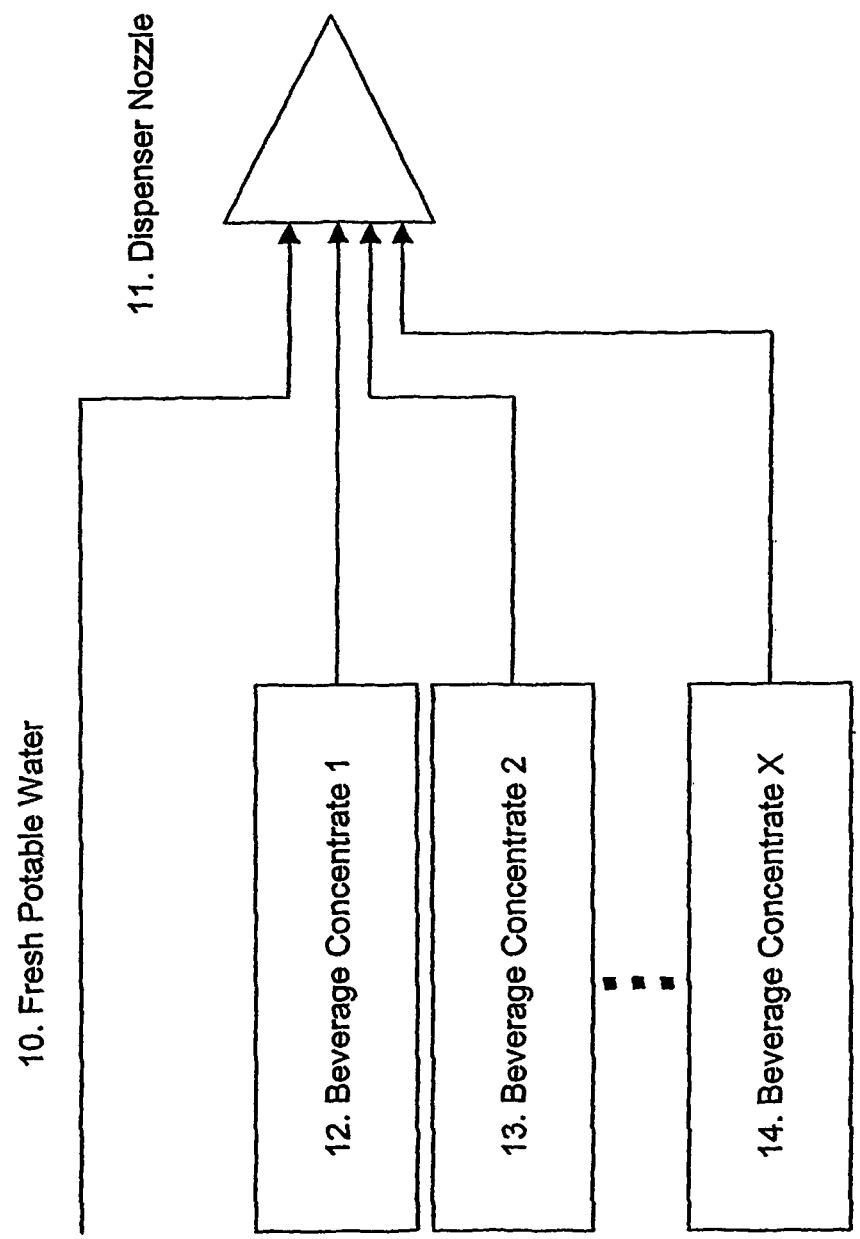
Figure 1. Typical Beverage Dispenser

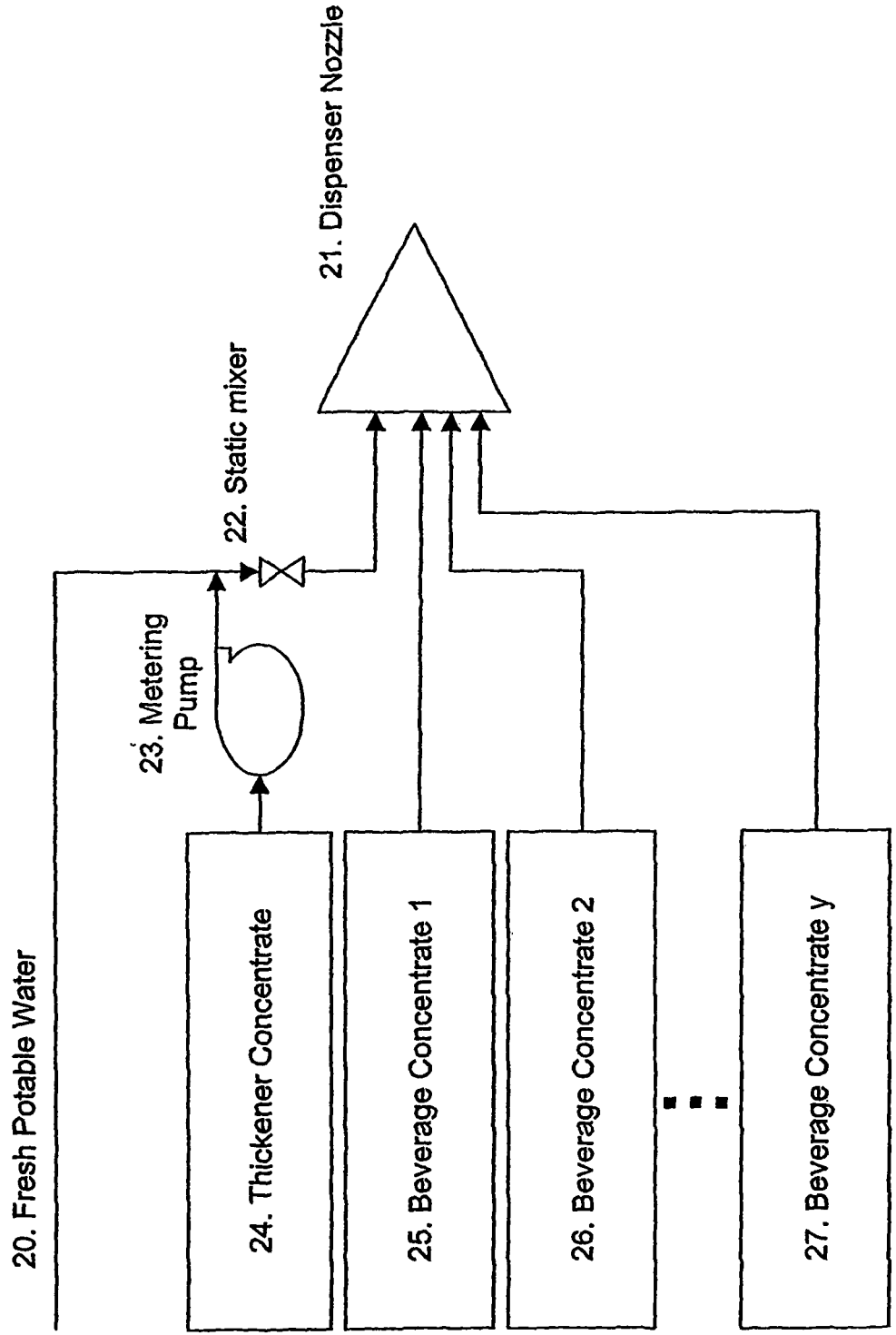

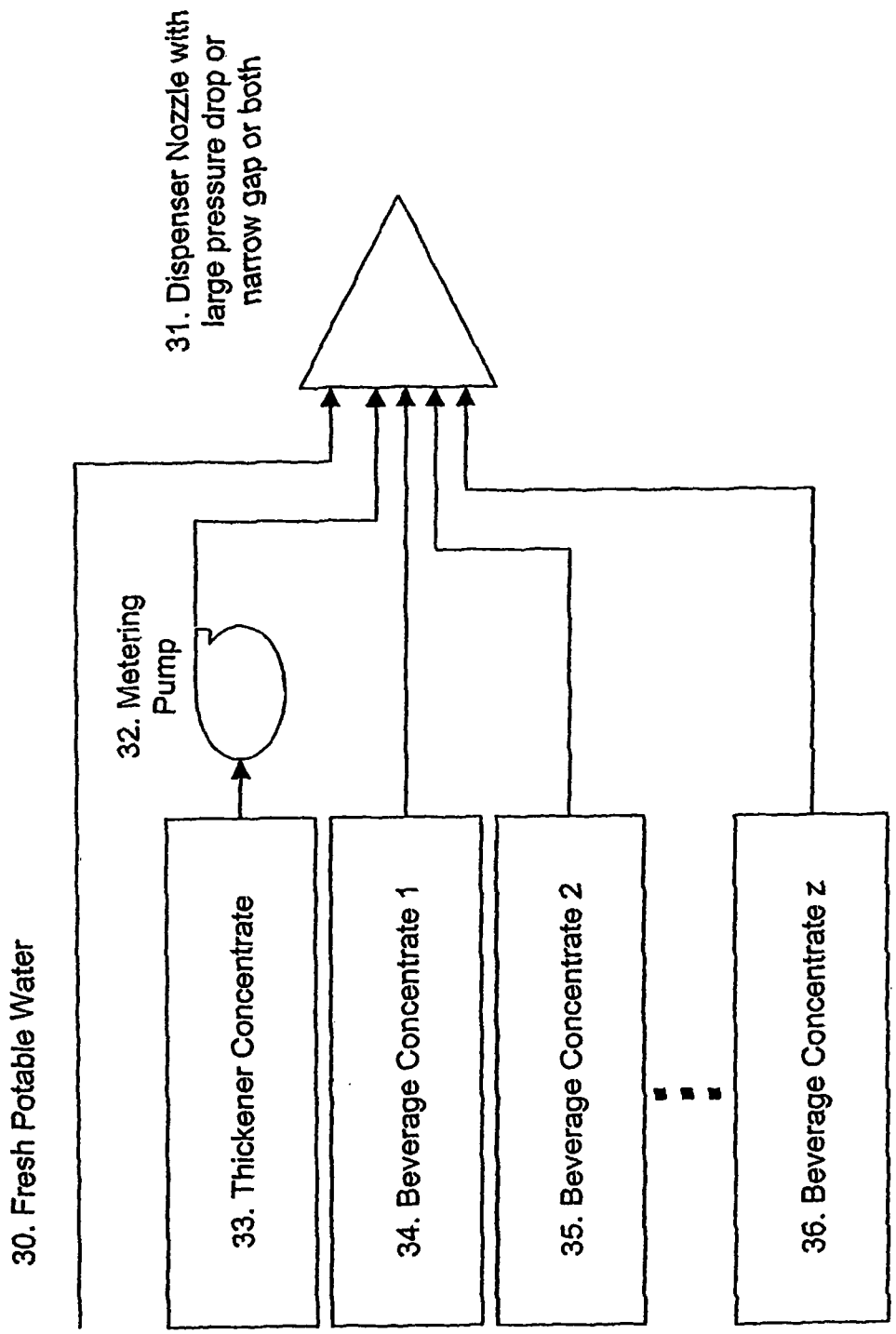

THICKENED BEVERAGES FOR DYSPHAGIA

CROSS REFERENCE TO RELATED APPLICATIONS

This application is the United States national stage filing of PCT/US04/002795, filed Jan. 31, 2004, which claims the individual and collective benefit of U.S. provisional application Ser. No. 60/444,079 filed Jan. 31, 2003, U.S. provisional patent application Ser. No. 60/443,941 filed Jan. 31, 2003, U.S. provisional patent application Ser. No. 60/444,080 filed Jan. 31, 2003 and U.S. provisional patent application Ser. No. 60/444,082 filed Jan. 31, 2003 each and all of which are incorporated herein in their entirety by reference.

FIELD OF THE INVENTION

This invention relates to thickened beverage compositions. More particularly this invention relates to enhanced thickened beverage compositions comprising xanthan gum which may be effectively administered to living humans to overcome a human swallowing difficulty.

BACKGROUND OF THE INVENTION

Swallowing problems in humans include difficulty in swallowing, inability to swallow, and discomfort in swallowing. These problems are collectively termed dysphagia. Dysphagia is a common unfortunate secondary condition that accompanies (i.e., is concomitant with) many primary human disease states such as at least one of blunt throat injury, surgery caused impairment, stroke, multiple sclerosis, asperger syndrome, esophageal cancer, laryngeal cancer, chagus disease, celiac, cystic fibrosis, Huntington's disease, Niemann-Pick disease, neurological conditions such as amyotrophic lateral sclerosis, Alzheimer's and Parkinson's disease, obesity, Riley-Day syndrome, high cholesterol, corn allergies and corn sensitivities, scleroderma, and diabetes.

Dysphagia is pervasive as between about five and about fifteen million people in the United States suffer from dysphagia. People with dysphagia generally lack proper muscle control and coordination to properly seal the windpipe or they lack the ability to properly propel the entire bolus of food and/or beverage to the stomach. If this condition goes unnoticed, sufferers are prone to foodstuff(s) and beverages going into the sufferer's lungs rather than being routed properly to their stomach. When routing to the lungs occurs, the patient sufferer is at increased risk for growing unhealthy bacteria in the lungs which raises the prospect of aspiration pneumonia (with its accompanying attendant risks and hospitalization) and/or even fatal asphyxiation.

Thickening the beverages of those humans afflicted with dysphagia is a common method of managing dysphagia. Thickening provides better bolus control, greater oral stimulation, and when swallowed, if incompletely propelled into the esophagus, it helps prevent undesired and potentially fatal aspiration of fluids into the lungs.

Generally and most commonly, starch is used to thicken beverages of dysphagia patients. This can either be accomplished manually at or near the point and time of service or it can be accomplished in a supplier's manufacturing facility. The former involves the addition of dry powder, agitation and time to achieve the thickness. The latter commonly is referred to as pre-thickened beverages.

It is highly desired to have a product for dysphagia sufferers which improves upon the current thickeners available to dysphagic patients to better and more completely meet all of their needs. Powders have serious problems in that they do not disperse well, leave powder clumps, do not thicken many beverages, and will continue to thicken over time after mixing.

In addition, unfortunately, starch also has several serious inherent problems that limit its usefulness in the management of dysphagia and/or limits its suitability to be used by those with dysphagia and other diseases. Starch is an easily digested carbohydrate. It adds calories to diets, and is thereby unsuitable for use with those who are on calorie restrictions, such as the morbidly obese. Starch consumption elevates blood sugars and can not be easily used by diabetics. Starch contains gluten that makes it unsuitable for those with celiac's disease. Ketogenic diets, which control epileptic seizures by limiting digestible carbohydrate consumption also are inappropriate for starch thickeners. Finally, the palatability of starch thickened beverages is poor, "Texture and Flavor Characteristics of Beverages Containing Commercial Thickening Agents for Dysphagia Diets", V. Lotong, Journal of Food Science, Vol. 68, Nr. 4, 2003, pp. 1537-1541. Patients have long complained of the poor appearance and taste of beverages prepared with starch and are inclined to resist drinking beverages. This can be especially problematic with patients of a young age or who have concomitant dementia or other impairment of cognitive communications.

Despite advances in the technology of food administration to patients, it is highly desired to have a composition which can be effectively administered to alleviate at least one of difficulty in swallowing, inability to swallow, and discomfort in swallowing to a dysphagic patient.

BRIEF DESCRIPTION OF THE INVENTION

In an aspect, the invention comprises an efficacious treatment for patients afflicted with concomitant dysphagia and a least one disease other than dysphagia or other injury using a soluble food fiber thickener to allow the patient to successfully swallow liquid foods.

In another aspect, an effective treatment for dysphagia comprises feeding pre-thickened liquid food compositions with aesthetic or composition or digestive properties or combinations thereof improved to dysphagic patients to provide for greater food consumption of the dysphagic patient.

In an aspect, a method for increasing liquid consumption of a patient afflicted with dysphagia comprises providing liquid foods to the patient, the food having been thickened with a thickener having improved taste and appearance.

In an aspect, a method for caring for a dysphagia patient at home or in an institution comprises feeding pre-thickened liquid food compositions with aesthetic or composition or digestive properties or combinations thereof improved to provide for greater consumption to a dysphagic patient.

In an aspect, a process for diagnosing and managing dysphagia comprises utilization of a consistent thickening system in both radiological compound(s) used for diagnosis and the thickened liquid foods ordered as a result of the radiological procedure.

In an aspect, a process for diagnosing and managing dysphagia which comprises utilization of a consistent rheology system, while allowing variation in the specific thickeners employed, in both the radiological compounds and the thickened liquid foods ordered as a result of the radiological procedure.

In an aspect, a medical facility comprising x-ray fluoroscopy facilities operated with radiological compounds and thickened liquid foods prepared in a manner such that their objective fluid characteristics are the same and the thickening system is generally the same.

In an aspect, a process for the production of homogeneously stable single phase thickened aqueous based beverages by a dispensing system suitably configured to produce such dispensed thickened multi-component beverages.

BRIEF DESCRIPTION OF THE DRAWINGS

FIG. 1 shows the operation of a beverage dispenser.

FIG. 2 shows a beverage dispenser configured to the present invention.

FIG. 3 shows a beverage dispenser with an alternative configuration of the present invention.

DETAILED DESCRIPTION OF THE DRAWINGS

FIG. 1 shows the operation of a beverage dispenser useful to prepare a thickened composition of this invention. In connection therewith, fresh potable water (10) enters dispenser nozzle (11) at the same time as one of the beverage concentrates (12, 13, 14). The flow rates are designed so that the appropriate ratio of water and concentrate exit the nozzle to produce a final beverage. There is not a permanent number of beverage concentrates (12, 13 and 14) attached to an individual nozzle, although it is typically more than 1 and less than 10. In an aspect, such as in FIG. 1, there are three shown for illustration purposes.

FIG. 2 shows a beverage dispenser configured to the present invention. Thickener concentrate (24) is delivered by metering pump (23) to fresh potable water (20) slightly before arriving at static in-line mixer (22). The metering pump (23) can deliver varying amounts of thickener concentrate (24) depending on what beverage will be made and the consistency to be made. In-line static mixer (22) completely mixes the thickener concentrate and fresh potable water. The thick stream arrives at the dispenser nozzle (21) at about or at the same time as one of the beverage concentrates (25, 26, 27). The flow rates are designed so that the appropriate ratio of water and concentrate exit the nozzle to produce the final beverage product. The nozzle is designed to provide enough agitation of the two streams to produce the final thickened beverage. Metering pump (23) may also not be activated for a particular beverage, so that a normal or unthickened beverage may be dispensed. There is not fixed number of beverage concentrates (25, 26, and 27) attached to an individual nozzle, although it is typically more than 1 and less than 10. In FIG. 2, three nozzles are shown for illustration purposes.

FIG. 3 shows a beverage dispenser with an alternative configuration of the present invention. Thickener concentrate (33) is delivered by metering pump (32) directly to the dispenser nozzle (31). Fresh potable water (30) and beverage concentrates (34, 35, and 36) also arrive directly to the dispenser nozzle (31). The metering pump (32) can deliver varying amounts of thickener concentrate (33) depending on what beverage will be made and the consistency to be made. Metering pump (32) may also not be activated for a particular beverage, so that a normal or unthickened beverage may be dispensed. The flow rates of fresh potable water (30), metering pump (32) and beverage concentrates (34, 35, and 36) are designed so that the appropriate ratio of water, thickener concentrate and beverage exit the nozzle to produce the final beverage. The dispenser nozzle (31) is designed to provide much agitation to combine the 3 stream completely. This is achieved most typically by a large pressure drop or a narrow gap or both. There is not a permanent number of beverage concentrates (34, 35, and 36) attached to an individual nozzle, although it is typically more than 1 and less than 10. In an aspect, such as shown in FIG. 3 for illustration purposes, three concentrates are added.

DETAILED DESCRIPTION OF THE INVENTION

The invention relates to methods of and to a system of preparing liquid diagnostic admixtures and liquid food compositions and to admixtures and compositions thickened for the management of dysphagia in living patients so afflicted. More particularly this invention relates to liquid food compositions thickened for dysphagia treatment and management of dysphagic patients that have improved aesthetics, composition, ease of use and/or digestion.

In an aspect, a specific thickener is chosen for a variety of reasons, including its aesthetic properties, its composition, its digestion properties, the equipment available to mix with, the cost of the formulation, the needs of specific patients to use the end product, other ingredients in the liquid foods to be thickened, process conditions such as the shear and/or temperature to which the liquid food will be exposed or combinations thereof.

In general, in an aspect, the food thickener is a soluble food fiber thickener and the amount of food thickener employed will depend greatly on the specific thickener chosen, its specific thickening properties, the processing equipment employed and the consistency to be achieved among other factors. In general, without implying limitation, in an aspect, the amount employed is between about 0.05% and about 10% thickener by weight. Most typically the amount employed will be between about 0.10% and about 2% thickener by weight.

The amount of thickener or the amounts of the thickeners used is generally that which is sufficient and efficacious for the particular liquid diagnostic or liquid food to attain a thickness useful in the treatment of persons afflicted with dysphagia. It is highly desired to avoid a too thick composition whereby a patient cannot effectively consume the composition due to the composition being too thick.

In an aspect, a ready-to-consume liquid food comprises xanthan gum in the range from about 0.01% to about 5% and preferably from about 0.1% to about 2% of the final ready-to-consume liquid food (wt %).

There are a variety of methods to get the thickened beverage to a useful thickness. The specific process to achieve the useful thickness is not critical to the invention. Without implying limitation, these include preparing a thickener concentrate in accordance with PCT/US02/24525 filed 2 Aug. 2002 [Publication No. 03/01151 A1] which is incorporated herein by reference in its entirety and then admixing the concentrate into a diagnostic composition and/or the liquid food or beverage. If desired a pre-thickened ready-to-consume liquid food can be manufactured or prepared in a manufacturing or preparation facility, packaged and shipped to where the beverage will be consumed. If desired, a pre-thickened ready-to-consume liquid diagnostic can be manufactured in a manufacturing facility, packaged, and shipped to where the liquid diagnostic will be consumed during a diagnostic procedure.

In an aspect, the thickener comprises xanthan gum whose concentration ranges from about 0.01% to about 5% by wt. of a final ready to drink liquid (water based) food and preferably from about 0.1% to about 2% of a final ready-to-consume liquid aqueous food.

The present invention provides the benefits gained by careful selection of the thickener to enhance the final diagnostic and management liquid consumed by the dysphagic patient. Thickeners suitable for use in the present invention share the characteristic that they are also considered soluble food fiber when consumed by humans and travel through the gastro-intestinal tract. There are several thickeners which are suitable. Exemplary thickeners, to be used alone or in combination, without implying limitation may include alginates (sodium, potassium, or ammonium slats), carrageenan, cellulosics such as sodium carboxymethylcellulose sodium, hydroxypropyl cellulose, hydroxypropyl methyl cellulose, galactomannans such as locust bean gum, guar gum and the like and xanthan gum.

A preferred food thickener is xanthan gum. Even more preferred is a clarified xanthan gum. Xanthan gum is manufactured and sold by CP Kelco of Wilmington, Del. USA as the Keltrol (R) family of products, Rhodia Food Ingredients of Cranbury, N.J. as the Rhodigel family of products, and Archer Daniels, Midland Company of Decatur, Ill. USA. Xanthan gum is a microbial polysaccharide produced by a pure culture aeorbic submerged fermentation of *xanthomonas campestris*. Xanthan gum is comprised of a backbone comprised of 1,4 linked D-glucose with trisaccharide side chains on alternating anhydroglucose units. The side chains are comprised of a glucuronic acid residue between two mannose units. Typically, xanthan gum forms cloudy solutions in water. Examples include Keltrol, Keltrol F, and Rhodigel. Clarified xanthan gum is treated by the manufacturer to form clear solutions in water by removing the remnants of the manufacturing process which produces the cloudy solution. Examples include Keltrol T, Keltrol RD, and Rhodigel Clear. Both forms are typically available as a powder of varying particle sizes.

Employing xanthan gum or any of the other suitable thickeners is advantageous in terms of calorie count, its lack of gluten, its suitability for low carbohydrate diets, and its lack of actual internal digestion when consumed. In an aspect, the composition of this invention provides for enhanced ingestion into the gastro-intestinal system of a living animal but not digestion of the thickener so employed therein.

Xanthan gum and the other suitable thickeners have several inherent physical properties that make it ideally suited for patients afflicted with dysphagia in general and with several concomitant ailments in particular. First, as mentioned previously, they are soluble food fiber. They are not really digested in the human gastrointestinal tract. Hence, they contribute little, if any calories to a food they thicken. Second, they do not contain corn or corn by-products. Finally, it is known that consumption of large amounts of soluble food fibers and xanthan gum in particular will reduce cholesterol levels (Eastwood, M. A. et al, The Dietary Effects of Xanthan Gum in Man, 1987). As a result of these properties, the use of thickeners of the present invention and use of xanthan gum in particular to thicken beverages for those afflicted with dysphagia are suitable for groups of dysphagia patients including patients with sensitivities to corn or corn products, or gluten do not react to beverages thickened with xanthan gum or the other suitable thickeners and patients who must limit their carbohydrate consumption, such as epileptic patients, and diabetics benefit from beverages thickened with suitable thickeners. Since the thickener is not digested, little, if any of its constituent carbohydrates can be absorbed into the body. This is ideal for ketogenic diets and diabetic diets. As used herein, ketogenic diet includes a diet used to treat seizures wherein fluids are limited and the diet is high in fat, and low in digestible carbohydrate and protein, which results in ketosis. The ketotic state is believed to exert a beneficial anti-epileptic effect.

As used herein the term "liquid food" includes a food, liquid in appearance, entirely or in part based on water, a liquid nutrient, food containing unbound liquid, liquid medication or food.

As used herein the term "liquid diagnostic" includes a diagnostic composition, liquid in appearance, entirely or in part based on water and a contrasting agent suitable for successfully detectably imaging the swallowing process of those afflicted with or suspected of having dysphagia. In an aspect, the contrast agent is barium sulfate.

As employed herein the term "juice" includes puree, fruit juices including orange juice, vegetable juice and apple juice strained and unstrained, concentrated and fresh.

Because thickeners of the present invention are not digested, they do not provide calories to the dysphagic patient's diet. For patients, such as living humans, who are on calorie restricted diets, administration of a composition of the present invention to these patients allows these patients to substitute food for the calories that starch thickeners would account for.

Patients with high cholesterol levels can see reductions in cholesterol levels when consuming adequate daily fluids with typical use levels of compositions of the present invention.

In an aspect, the food thickeners useful in of the present invention share similar characteristics to xanthan gum in their aesthetic, composition, and digestion.

In an aspect, a single food thickener selected from the list above may be admixed with a liquid food to produce a ready-to-consume beverage that is already thickened to a useful level for use in the management of dysphagia when the package is open. The advantage here is that all of the dietary benefits mentioned above. In addition, by carefully selecting the thickener used, it is also possible to make a more visually appealing and better tasting ready-to-consume liquid food. Starch leaves beverages milky and cloudy with a starchy metallic taste. This can be especially troubling to patients in a beverage that they expect to be able to see through, such as water. Certain grades of xanthan gum and cellulosics, for example, produce clear solutions when dissolved and to not impart negative flavors. Being able to produce clear better tasting liquid foods is a real benefit for patient acceptance.

In an aspect, a single food thickener may be used or combinations thereof may be employed. The exact choice of the thickener used will be based on a variety of factors such as the equipment available to mix with, the cost of the formulation, the needs of specific patients to use the end product, other ingredients in the liquid food, process conditions such as the shear and/or temperature to which the liquid food will be exposed. Illustrative and nonlimiting examples of such thickeners have been mentioned previously. In a preferred aspect, the thickener selected comprises xanthan gum.

The amount of food thickener employed will depend greatly on the specific thickener chosen, its specific thickening properties, the processing equipment employed and the consistency to be achieved. In general, the amount employed will be between about 0.05% and about 10% thickener by weight. Most typically the amount employed will be between about 0.10% and about 2% thickener by weight.

In an aspect, a sufficient quantity of thickener powder for the solution being prepared is admixed with the liquid food to be thickened in a suitable mixing vessel. A preferred mixing vessel comprises a container which is of a size accommodating the amounts of thickener powder and liquid food desired to be suitably mixed. The vessel typically is a commercially sized tank, the particulars of which are not critical and may or may not include a cover, a particular shape, the presence of baffles, and/or a heat jacket. Any suitably sized container which will accommodate the amount of liquid food and food thickener to be suitably admixed is appropriate is within the scope of the present invention.

Generally, due to the choice of thickener, the temperature of the liquid food is not critical to the preparation of the thickened beverage and may include, without limitation hot, cold, or room temperature liquid foods. With some particular thickeners, the inherent properties will make the choice of temperature more critical or sensitive than it is with others. These situations will be obvious to those skilled in the art of making thickener solutions.

As necessary or desired, minor components such as acids, acidulates, chelating agents, flavors, juice or other concentrates, colors, vitamins, minerals, and/or preservatives may be incorporated into the thickener and liquid food admixture at any appropriate point during the preparation. It is understood that such minor components will likely be present in minor amounts and concentrations, i.e. a non-substantial amount as relates to thickening.

The order of addition of ingredients is not necessarily important. Generally, the ingredients are added in a manner to most effectively and efficiently prepare the pre-thickened ready-to-consume liquid food with the equipment being used. However, in certain instances, without limiting the scope of the present invention, the specific thickener being employed may benefit from a specific order of addition. An example is that cellulosics will create the greatest amount of thickening when first added to plain water and dissolved. Then the other ingredients, including juice concentrates, can be added. These situations will be obvious to those skilled in the art of making thickener solutions.

Depending on the specific admixing equipment used and the appropriate handling of the materials is an exemplary embodiment, the time needed for admixing is in the range from about 2 minutes to about 180 minutes and preferably from about 5 minutes to about 60 minutes although greater and lesser times may be employed if desired or necessary.

Optionally, as necessary or desired for shelf life, the thickened liquid food may be treated to provide shelf stability. Most commonly, but not limiting, the treatment is an effective amount of heat in combination with some of one or more of one or more of the minor ingredients mentioned above.

Packaging of the ready-to-consume thickened liquid food is not critical as long as the packaging delivers the liquid food effectively. Illustratively, packaging may be bottles, jars, cups, scholle bags, packets, pouches, Tetra Paks, or the like.

In a further aspect the preparation of a thickener concentrate facilitates in-line mixing and preparation of thickened liquid foods in a beverage dispenser or container. In an aspect, such a system would include a metering device and an in-line mixing system to dispense thickened liquid foods. In an aspect, a system is configured to dispense thickened or non-thickened liquid foods at the turn of a switch. Being able to serve thickened and unthickened liquid foods is especially advantageous over the current state of affairs where thickened and unthickened liquid foods are stored and prepared separately.

Beverage dispensers are mixing devices which combine a fresh water feed with concentrates to make a final beverage. (See FIG. 1 for an illustrative example.) Each stream meets at the nozzle and the nozzle design mixes the streams together to make the final beverage.

In an aspect, an effective amount of a thickener concentrate is prepared and packaged in a suitable container for use with a beverage dispenser.

The amount of thickener employed in a concentrate thickener will depend greatly on the specific thickener chosen, its specific thickening properties, and the processing equipment employed. In general, the amount employed will be an effective amount, such as between about 1 and about 10% thickener by weight. Most typically the amount employed will be between about 1 and about 5% thickener by weight.

The concentration may vary depending on the equipment and the thickener employed. In an aspect, a sufficient quantity of thickener powder for the concentrate thickener being prepared is admixed with water in a suitable mixing vessel. A preferred mixing vessel comprises a container which is of a size reasonably accommodating the amounts of thickener powder and water desired to be suitably mixed. The vessel typically is a commercially sized tank, the particulars of which are not critical and may or may not include a cover, a particular shape, the presence of baffles, and/or a heat jacket. Other suitable useful mixing vessels include a drinking cup, bowls, household containers which can be open or closed top, a kitchen top mixer system, as well as any suitably sized container which will accommodate the amount of water and thickener to be suitably admixed.

Generally, the temperature of the water is not critical to the preparation of the concentrate thickener and may include, without limitation hot, cold, or room temperature water suitable for human consumption. With some thickeners, the inherent properties will make the choice of temperature more important than it is with others.

As necessary or desired, one or more minor components such as acids, bases, acidulates, chelating agents, flavors, colors, vitamins, minerals, sweeteners, insoluble foods and/or preservatives may be incorporated into the thickener and water admixture at any appropriate point during the preparation. It is understood that such minor components will likely be present in minor amounts and concentrations, i.e. a non-substantial amount as relates to thickening.

In an embodiment, depending on the specific admixing equipment used and the appropriate handling of the materials the time needed for admixing the thickener concentrate is in the range from about 2 minutes to about 180 minutes and preferably from about 5 minutes to about 60 minutes although greater and lesser times may be employed if desired or necessary.

Optionally, as necessary or desired, the thickener concentrate may be treated to provide shelf stability. Most commonly, but not limiting, the treatment is heat in combination with one or more of the minor components mentioned above.

The packaging of the thickener concentrate is not critical as long as it can be connected to a beverage dispenser and delivers an effective amount of concentrate to thicken a liquid food to a thickness effective for a person afflicted with dysphagia. Illustratively, packaging may be totes, bins, foil pouches, buckets, bags, syringes and the like.

Use of a thickener concentrate will facilitate in-line mixing and preparation of thickened beverages in a beverage dispenser or container. Such a system includes a metering device and an in-line mixing system to dispense thickened beverages. It could also be designed to dispense thickened or non-thickened beverages at the turn of a switch or the push of a button.

In an aspect, the thickener concentrate is an effective thickener for liquid foods.

In an exemplary process, the amount of thickener concentrate employed in the admixture is that amount which provides a thickened liquid food which is capable of being consumed by effectively swallowing by a person afflicted with dysphagia.

In an aspect, the packaged concentrate is connected to a metering pump. Most often, but not necessarily, the metering pump will be located within the beverage dispenser itself. When the dispenser is activated, the metering pump delivers the thickener concentrate at an appropriate rate to produce the desired consistency and desired flavor of beverage. The appropriate streams of fresh water, thickener concentrate, and optional juice concentrate are mixed and delivered to the awaiting container. Once dispensed, the beverage is immediately ready to be consumed and will not thicken upon standing.

In an aspect, the concentrate is connected to a metering pump that is capable of accurately metering the concentrate solution. Typically this will involve a progressive cavity displacement pump. As a non-limiting example, Moyno, Inc., Springfield, Ohio, USA, manufactures a range of such metering pumps.

In an aspect, the metering pump is activated by the dispenser, the particulars of which are not important. It is only important that the pump is activated (i.e., operated) and that it meters an appropriate amount of the thickener concentrate for the thickness that is to be prepared. As a non-limiting example, a thickener concentrate prepared with 3.75% xanthan gum would need to be metered at a rate of 25 g of concentrate for every 145 g of total fluid prepared to make a honey-consistency. The same concentrate would need to be metered at 10 g of concentrate per 130 g of total beverage prepared to achieve a nectar consistency.

The stream of thickener concentrate exits the metering pump and is mixed into the other beverage components, most typically water and optionally a juice concentrate, producing the ready to serve thickened beverage. Non-limiting examples are illustrated in FIGS. 2 and 3 and are described above.

In FIG. 2, the thickener concentrate is effectively combined with the incoming fresh potable water and the two streams are mixed in-line with a static in-line mixer. The thickened water is then ready to drink or is combined with a beverage concentrate at the nozzle to produce the final ready-to-consume thickened beverage for a dysphagic patient.

In FIG. 3, the thickener concentrate, water and optional beverage concentrate are all effectively pumped directly to the nozzle. They are combined in the nozzle and the mixing action is a result of the nozzle design. Typical nozzle designs that would work with this system have a high pressure drop or a narrow gap to pump through or both. The final beverage exits the nozzle as a ready-to-consume thickened beverage for a dysphagic patient.

In an aspect an in-line mixing device is installed and functionally connected with the process piping to provide continuous mixing for blending of two or more ingredients such as illustrated in FIGS. 1, 2, and 3. In an aspect, the mixing or integration of the several ingredients into a single multicomponent homogenous aqueous composition is carried out in a computer controlled system, which is generally termed an automatic system. In an aspect the number of ingredients ranges from two to about five, although a greater number of ingredients and mixtures and compositions may be employed if desired. In an aspect the various ingredients are fed to the in-line mixer and the mixed product exits the mixer.

In an aspect the in-line mixing device comprises a static (motionless) mixer having a mixer body composition selected from one of flexible plastic, fiberglass and stainless steel composition. In a further aspect the wetted parts would be mechanically polished to specification with variable speed controls provided. In an aspect the material of composition will be selected to be process compatible with the ingredients to be mixed and the mixed product.

Generally such static mixers work by dividing streams of ingredients that need to be mixed. The ingredient stream typically is forced through the static mixer by action of a pump. The ingredients to be mixed are split into substreams internal to the mixer as they are forced through the mixer as substreams. These substreams are then recombined and divided once again in a repetitive fashion. In an aspect, baffles may be used to divide ingredients into two or more streams but some static mixing designs divide ingredients into four streams which are then recombined. The in-line mixing may be carried out in a batch, continuous or semi-continuous mode and as part of an automated system.

If desired the pumps are self priming and water solenoid valves feed the ingredients and water in a precise volume determined by preset volumes. The mix quantities, sequences and mix times are programmed into a memory chip and the precise quantities of each constitutes are set by software adjustment from the keyboard of the system configurably connected to a computer controlling the process.

In an aspect a progressive cavity pump moves the various ingredients through the mixing process with the pumps providing the mixer with a meter uniform flow. In an aspect an individual pump is employed for each ingredient.

In an aspect a mass flowmeter is employed to control the amount of each ingredient into the composition which provide feedback to the pumps to ensure accurate delivery of the ingredients. A user then may enter the proportions of each component into a computer associated with this process and the control loop provided by the computer (with software) ensures that each ingredient is provided accurately. An in-line heater may be employed if desired.

In an aspect, an operational computer equipped with configurable software, such as a PC, controls the process as it controls the mixing machine, pumps mixing time, mixing temperature and other corresponding process control variables.

In an aspect a motion type in-line mixing device is employed having various impeller styles and sizes are available which are configured to produce the desired homogeneity of the product composition.

A variety of some useful in-line mixers are listed in the Thomas Register Directory. If desired a mixing pump may be employed including an inpump mixing system.

In an aspect, the final material leaving the mixing device will be a homogenous, single phase liquid food, whether thickened or not. If thickened using the thickener concentrate and metering pump, the beverage will be free (or at least substantially free) of discontinuities such as unmixed unblended areas of thickener concentrate, often referred to as 'fish eyes'. The thickened liquid food will be completely thickened at the appropriate thickness sufficiently thickened and ready-to-consume at that time. Advantageously the thickened liquid will not continue to thicken on standing or provide any indication that it is not mixed thoroughly. The compositions herein advantageously provide a consistent stable homogeneity from the time of preparation through use. So, in essence, what you have made is what you provide to a patient.

Advantageously, this invention provides a link which assures dysphagia suffers that the thicknesses used for aqueous liquids during the radiologic procedures match those of their treatments. Thus, in this invention, diagnosis compounds created on-site in the radiologic suite simulate a thickness that the person administering the test thinks appears correct. The compounds of the present invention allow a link between the radiology suite and the thickened compounds served on a daily basis to treat patients.

This link provides an advantage by this invention and starts in the diagnostic stages of dysphagia and is particularly useful in the overall care and disease management for the dysphagic patient. The most common diagnostic procedure is a modified barium swallow which is administered under x-ray fluoroscopy. As used herein the term "fluoroscopy" includes a form of diagnostic radiology that enables the radiologist, with the aid of a contrast agent, to visualize an organ or area of concern of a patient via x-ray. Although fluoroscopic exams may be done of the stomach and esophagus, small bowel and upper GI, within this invention, the areas of most concern to an attending physician or other medical professionals are the head and neck regions of the patient's body. The contrast agent allows the image to be viewed clearly on a monitor or screen. Contrast agents (or "contrast media" as they are also known) are introduced into the body through swallowing. In an aspect each fluoroscopic examination comprises a series of images taken by the radiologist.

In an aspect, the x-ray diagnostic system comprises a vital part of a comprehensive assessment program available to persons in an outpatient or inpatient setting and is especially valuable to those whose physical, functional, or emotional status has become unstable. Such a system is of vital importance to dysphagic patients. This system is also of value in a care program which offer a variety of services including at least one of assisted living, long term care, community living, at-home clinical care, end-of-life home care, hospice, caregiver education, respite and home-maker visits.

In accordance with an embodiment of the invention, admixtures are prepared which result in a liquid radiologic diagnostic preparation and/or a liquid food preparation. Although either composition can be prepared at the same time or more preferably they can be prepared independently, they are of a similar thickness and similar rheology. Without limiting any scope of this invention, an example of why these liquid admixture would be prepared independently is that the liquid diagnostic can be prepared by a medical professional just prior to the diagnostic procedure and the liquid food can be prepared at a later time at home by a caregiver. An essential advantage and feature of this invention is that the thickness and rheology of the compounds are similar, thereby ensuring that the diagnostic liquids better simulate the liquid foods prepared for dysphagia management. There are several thickeners which are suitable. Exemplary thickeners, to be used alone or in combination, without implying limitation may include alginates (sodium, potassium, or ammonium salts), carrageenan, cellulosics such as sodium carboxymethylcellulose sodium, hydroxypropyl cellulose, hydroxypropyl methyl cellulose, galactomannans such as locust bean gum, guar gum and the like and xanthan gum. In a preferred aspect, the thickener selected comprises xanthan gum.

Diagnosis of the proper treatment for dysphagia is often done using a radiologic procedure known as the modified barium swallow. Barium sulfate suspensions of various thicknesses are served to patients while an x-ray fluoroscope is used to record the patient's ability to swallow these compositions.

Additionally, this invention is useful in increasing the food intake in assisted care, elder care, hospital and nursing home patients who in increasing numbers lately are showing reductions in food intake. The inventive method herein is quite useful in assisting patients with their eating aspect which is a main activity among the six activities of daily living (ADL's). Poor flavor, appearance and sensory perception of starch thickeners lead to poor fluid consumption. Using the inventive methods herein will improve the appearance and flavor of the beverages served to dysphagic patients leading to consequent increases in fluid consumption.

In an aspect, this invention is useful to treat dysphagia which a living human disease state including blunt throat injury, surgical impairment, stroke, multiple sclerosis, Asperger syndrome, esophageal cancer, laryngeal cancer, Chagas disease, cystic fibrosis, Huntington's disease, Niemann-Pick disease, amyotrophic lateral sclerosis, Parkinson's disease, Riley-Day syndrome, scleroderma and Alzheimer's disease and perhaps surgery and blunt injury Although exemplary embodiments of processes are described herein, processes are not limited to such exemplary embodiments.

EXAMPLES

Examples 1 and 2 demonstrate that effective thickened liquid foods with lower calories and higher food fiber can be prepared with xanthan gum.

Example 1

A ready-to-consume pre-thickened type of thickened liquid food was prepared with xanthan gum and compared to a commercially available ready-to-consume pre-thickened non-xanthan gum beverage to demonstrate the improvements in calorie counts and carbohydrate content of the xanthan gum composition.

In that regard, a thickened water was prepared to honey consistency with xanthan gum. 7 g of Keltrol T from CP Kelco was added approximately 250 mL of hot tap water (about 115° Fahrenheit) while mixing with an electric hand mixer with a whisk attachment. The mixing was stopped after approximately 2 minutes and the mixture was added to enough hot tap water to bring the total weight to 1080 g. in a stand mixer with a whisk attachment. The beverage was mixed for approximately another 15 minutes to ensure complete dissolution. The mixture was packed in both a glass jar and in a plastic bag. Using standard dietary methods, it was found that an 8 oz serving of the beverage of this example had the following characteristics. For comparison, similar information from a commercially available pre-thickened water from Novartis Nutrition, Minneapolis, Minn. is shown.

|  | Xanthan Gum | Commercial Product |
| --- | --- | --- |
| Calories | 0 | 80 |
| Carbohydrate | 1.5 g | 19 g |
| Sugars | 0 g | 8 g |
| Fiber | 1.5 g | 0 g | g = grams

Example 2

A xanthan gum thickener concentrate was prepared and its affect on water was compared to 2 commercially available starch products in 8 oz of water to show the reduction in calories and carbohydrate content. The concentrate was composed of 3.75% water, 0.5% citric acid, 0.1% sodium benzoate, and 0.1% potassium sorbate. The concentrate was heat processed for stability and stored in 10 g and 25 g foil packets. One 10 g packet was added per 4 oz of water for nectar consistency and one 25 g packet was added per 4 oz of water for honey consistency. For comparison, data were also collected from commercially available thickener powders known as ThickenUp from Novartis Nutrition, Minneapolis, Minn. and Thick-It from Precision Foods, St. Louis, Mo., USA.

| Thickener | Nectar Consistency | | Honey Consistency | |
|---|---|---|---|---|
| | Carbohydrate | Calories | Carbohydrate | Calories |
| Xanthan Concentrate | <1 g | 0 | 1 g | 5 |
| Thicken Up | 10.3 g | 40 | 12 g | 45 |
| Thick-It | 10.5 g | 53 | 17.5 g | 88 |

Example 3

Example 3 demonstrates the utility of a thickener system used for both liquid diagnostic compositions and liquid foods. A thickener concentrate of 3.75% xanthan gum was prepared with a preservative system of 0.25% citric acid, 0.1% sodium benzoate, and 0.1% potassium sorbate. The solution was packaged in foil packets of approximately 25 g and heat pasteurized for shelf stability. Approximately 6 months later, one 25 g packet of the concentrate thickener was added to 12 oz of a liquid barium sulfate suspension suitable for a modified barium swallow, Liquid E-Z-Paque from E-Z-EM Canada, Inc. The concentrate was also added to commercially available apple juice at a rate of one 25 g packet per 4 oz. of juice. Both solutions were deemed to be of honey consistency. The data are presented in the table below.

| | 100 rpm | 20 rpm | 5 rpm |
|---|---|---|---|
| Liquid E-Z-Paque | 450 cP | 1465 cP | 4220 cP |
| Apple Juice | 415 cP | 1550 cP | 4860 cP | cP = centipoise

The close agreement of viscosity at three different spindle speeds confirms that the solutions not only are the same consistency, but that they in fact have the same rheology and will perform the same when swallowed.

Examples 4-6 following demonstrate that effective thickened liquid foods with better taste and appearance can be prepared from xanthan gum.

Example 4

A ready-to-consume (eat by swallowing) thickened water was prepared to honey consistency with xanthan gum. 7 g of Keltrol T from CP Kelco was added approximately 250 mL of hot tap water (about 115 degrees Fahrenheit) while mixing with an electric hand mixer with a whisk attachment. The mixing was stopped after approximately 2 minutes and the mixture was added to enough hot tap water to bring the total weight to 1080 g. in a stand mixer with a whisk attachment. The beverage was mixed for approximately another 15 minutes to ensure complete dissolution. The mixture was divided into two portions. One was packed in a glass jar and the other in a plastic bag. Both were heat pasteurized. After 2 days, portions of the thickened water prepared as described along with portions of 3 commercially available honey consistency waters were served to 3 people in a blind test. The best scores for the best overall taste and the scores for the best overall appearance were for the xanthan gum product:

| Product | Avg Score, Taste (1 = best, 4 = worst) | Average Score, Appearance (1 = best, 4 = worst) |
|---|---|---|
| Xanthan gum | 2.0 | 1.0 |
| Resource | 2.3 | 2.7 |
| Hormel | 2.3 | 3.7 |
| Lyons | 3.3 | 2.7 |

Example 5

A ready-to-consume thickened cranberry juice cocktail was prepared to nectar consistency with xanthan gum. 3 g of Keltrol T from CP Kelco was added approximately 250 mL of room temperature tap water while mixing with an electric hand mixer with a whisk attachment. The mixing was stopped after approximately 2 minutes and the mixture was added to a further approximately 500 mL. The beverage was mixed for approximately another 20 minutes to ensure complete dissolution. Then 250 mL of a cranberry juice cocktail concentrate was added and mixed another 5 minutes. The mixture was divided into two portions. One was packed in a glass jar and the other in a plastic bag. Both were heat pasteurized. After 2 days, portions of the thickened cranberry juice cocktail prepared as described along with portions of a commercially available nectar consistency cranberry juice product were served to 3 people in a blind test. All 3 picked the xanthan gum mixture to be the best in appearance. All 3 picked the xanthan gum as the best tasting product.

Example 6

A ready-to-consume thickened apple juice was prepared to honey consistency with xanthan gum. 7 g of Keltrol T from CP Kelco was added to approximately 250 mL of room temperature tap water while mixing with an electric hand mixer with a whisk attachment. The mixing was stopped after approximately 2 minutes and the mixture was added to a further approximately 500 mL of water. The beverage was mixed for approximately another 20 minutes to ensure complete dissolution. Then 250 mL of an apple juice concentrate was added and mixed another 5 minutes. The mixture was divided into two portions. One portion was packed in a glass jar and the other portion was packed in a plastic bag. Both packed portions were heat pasteurized. After 2 days, portions of the thickened apple juice prepared as described along with portions of a commercially available honey consistency apple juice product were served to three people in a blind test. All three people picked the xanthan gum mixture to be the best in appearance. Two of the three picked the xanthan gum mixture as the best tasting product.

While the invention has been described in terms of various embodiments, those of skill in the art will recognize that the invention can be practiced with modification within the spirit and scope of the claims.

What is claimed is:

1. A process for the production of homogenous single phase thickened beverages suitable for consumption by a person suffering from dysphagia, the process comprising connecting a source of thickener concentrate to a dispensing machine that is capable of dispensing non-thickened beverages.

2. A process in accordance with claim 1 wherein the dispensing machine includes a container of thickener concentrate, a switch which selectively controls whether or not the thickener concentrate is included in the beverage, and a metering pump and an in-line static mixer connected to the container of thickener concentrate and designed such that beverages exit the dispenser at the correct thickness, with a homogenous appearance and are ready to drink, whether the beverage thickness is increased by inclusion of the thickener concentrate or not.

3. A process in accordance with claim 1 wherein the dispensing machine includes a container of thickener concentrate, a switch which selectively controls whether or not the thickener concentrate is included in the beverage, a metering pump, and an exit nozzle, the exit nozzle producing sufficient pressure drop that beverages exit the dispenser at the correct thickness, with a homogenous appearance and are ready to drink, whether the beverage thickness is increased by inclusion of the thickener concentrate or not.

4. A process in accordance with claim 1 wherein the thickener concentrate comprises at least one soluble food fiber thickener selected from the group consisting of sodium alginate, potassium alginate, ammonium alginate, carrageenan, sodium carboxymethylcellulose, hydroxypropyl cellulose, hydroxypropyl methyl cellulose, locust bean gum, guar gum, and xanthan gum.

5. A process in accordance with claim 4 where the thickener is xanthan gum.

6. A process in accordance with claim 5 where the xanthan gum is between 1% and 10% of the thickener concentrate.

7. A process in accordance with claim 5 where the xanthan gum is between 0.3% and 1% of the beverage.

* * * * *